US009623175B2

(12) United States Patent
Fini et al.

(10) Patent No.: US 9,623,175 B2
(45) Date of Patent: Apr. 18, 2017

(54) TUBING SET HAVING A GATE FOR THE CONNECTION OF VIALS

(75) Inventors: Massimo Fini, Mirandola (IT); Alain Veneroni, Spino d' Adda (IT)

(73) Assignee: PRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 834 days.

(21) Appl. No.: 13/696,892

(22) PCT Filed: Mar. 16, 2011

(86) PCT No.: PCT/EP2011/053936
§ 371 (c)(1),
(2), (4) Date: Nov. 8, 2012

(87) PCT Pub. No.: WO2011/141200
PCT Pub. Date: Nov. 17, 2011

(65) Prior Publication Data
US 2013/0060226 A1    Mar. 7, 2013

(30) Foreign Application Priority Data
May 14, 2010    (EP) .................................... 10162845

(51) Int. Cl.
*A61M 5/00* (2006.01)
*A61M 5/162* (2006.01)
(52) U.S. Cl.
CPC ..... *A61M 5/162* (2013.01); *A61M 2005/1623* (2013.01)

(58) Field of Classification Search
CPC ........ A61J 2001/2062; A61J 2001/2003; A61J 2001/2037; A61M 2005/1623; A61M 5/162
USPC ...... 604/6.11, 6.16, 151, 247, 403, 406–407, 604/411, 414, 500, 507
See application file for complete search history.

(56) References Cited

U.S. PATENT DOCUMENTS

| 4,381,776 A | * | 5/1983 | Latham, Jr. | A61J 1/05 128/DIG. 24 |
| 4,580,927 A | * | 4/1986 | Weeks | 406/50 |
| 4,673,404 A | * | 6/1987 | Gustavsson | A61J 1/2096 604/411 |
| 5,302,348 A | * | 4/1994 | Cusack et al. | 422/73 |

(Continued)

FOREIGN PATENT DOCUMENTS

| DE | 195 16 493 | 11/1996 |
| DE | 295 12 323 | 12/1996 |

(Continued)

*Primary Examiner* — Leslie Deak
*Assistant Examiner* — Kai Weng
(74) *Attorney, Agent, or Firm* — Jacobson Holman, PLLC

(57) ABSTRACT

A tubing set suitable for use in co-operation with a medical liquid delivery device includes a delivery tube configured to supply a medical liquid or blood to a patient, and a vial gate for the connection of vials containing drugs to be delivered into the medical liquid or blood. The vial gate includes a delivery lumen configured to deliver the drug from the vial to the delivery tube, and a vent lumen configured to deliver a replacement fluid from a location inside the tubing set to the inside of the vial in order to replace the delivered drug. The vial gate also includes at least one one-way valve placed along the vent lumen or the delivery lumen.

26 Claims, 12 Drawing Sheets

(56) References Cited

U.S. PATENT DOCUMENTS

| | | | |
|---|---|---|---|
| 6,017,493 A * | 1/2000 | Cambron et al. | 422/44 |
| 7,086,431 B2 * | 8/2006 | D'Antonio et al. | 141/330 |
| 7,572,489 B2 | 8/2009 | Dröschel et al. | |
| 2002/0115981 A1 | 8/2002 | Wessmann | |
| 2007/0106244 A1 * | 5/2007 | Mosler | A61J 1/2096 604/411 |
| 2007/0244456 A1 * | 10/2007 | Fangrow | 604/411 |

FOREIGN PATENT DOCUMENTS

| | | |
|---|---|---|
| EP | 0 001 114 | 3/1979 |
| EP | 0 637 971 | 2/1995 |
| EP | 2 319 553 | 5/2011 |
| IT | TO 2009A000445 | 12/2010 |
| JP | 2002-248166 | 9/2002 |
| WO | WO 87/75159 | 12/1987 |

\* cited by examiner

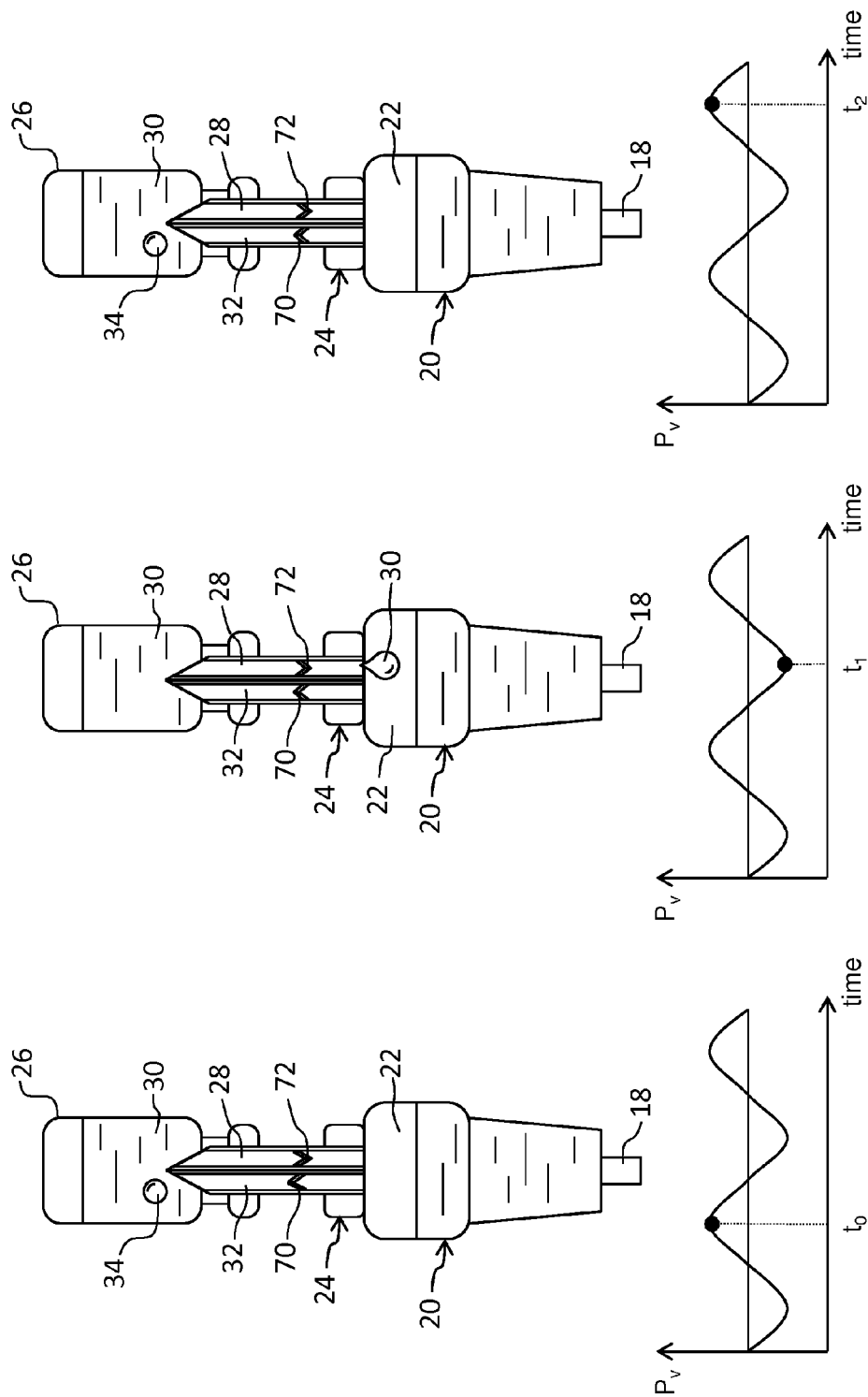

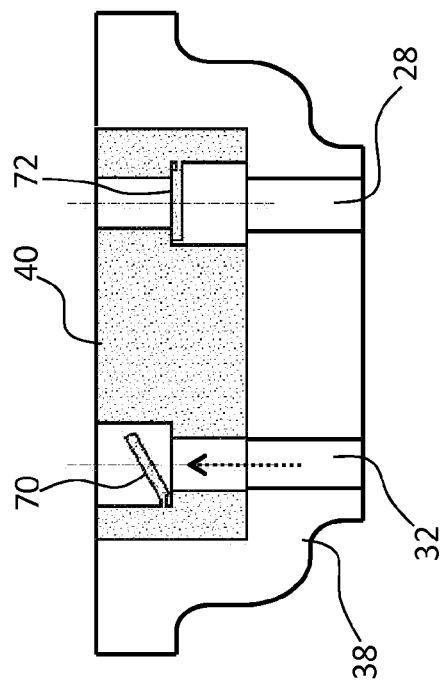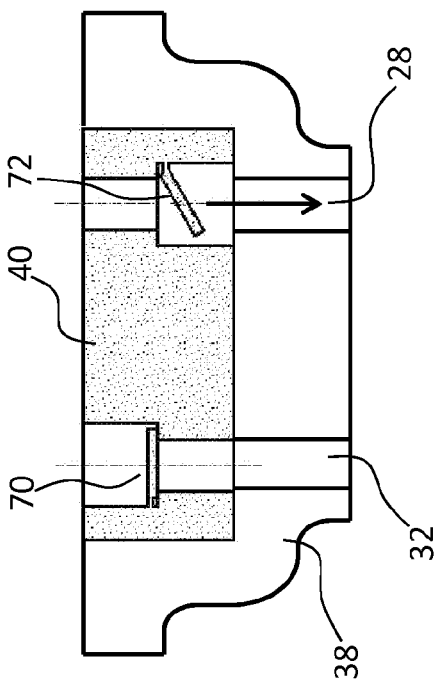
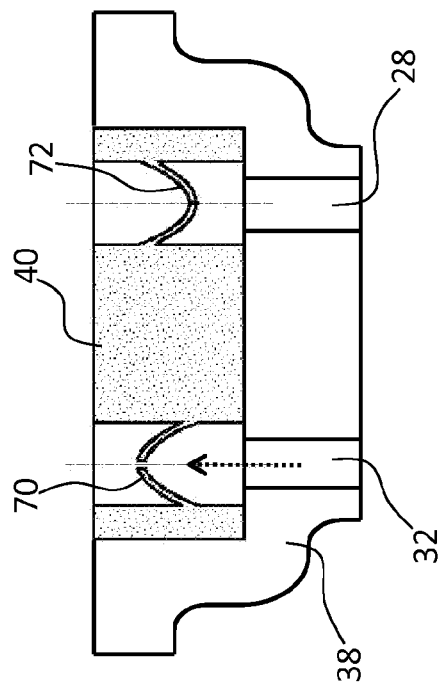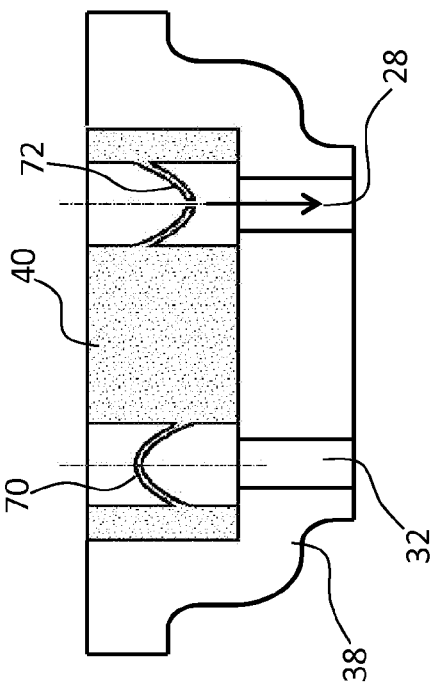

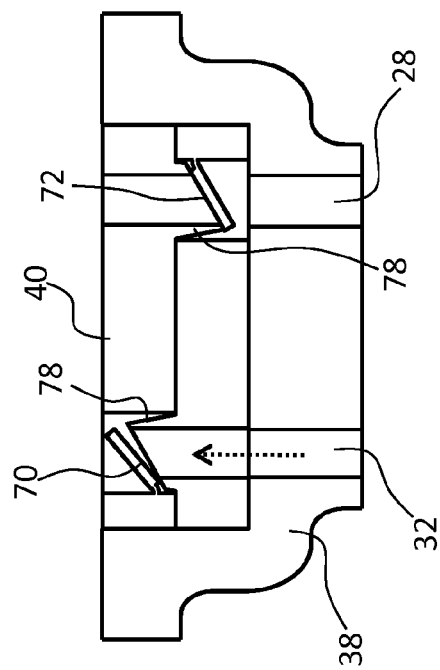
Fig. 16.a
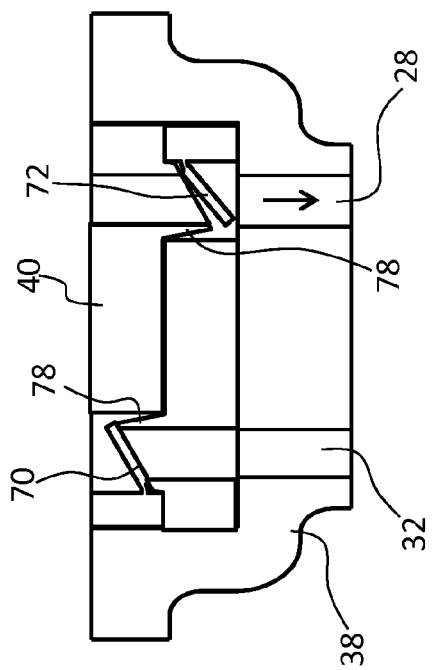
Fig. 16.b
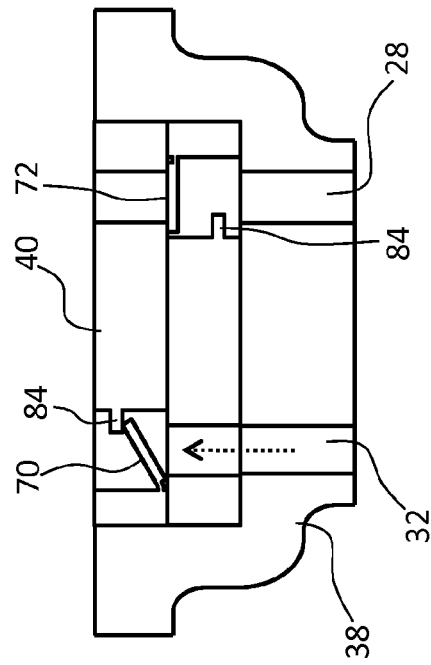
Fig. 17.a
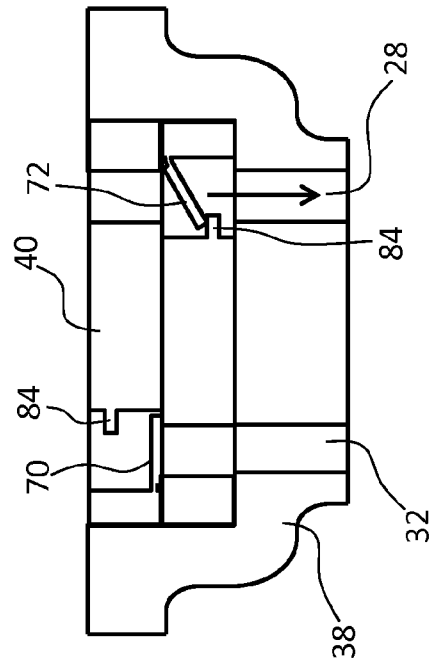
Fig. 17.b

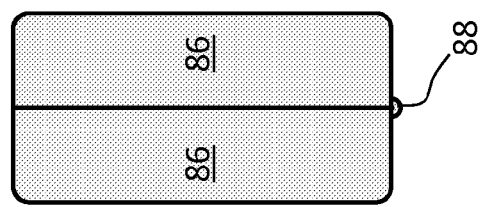
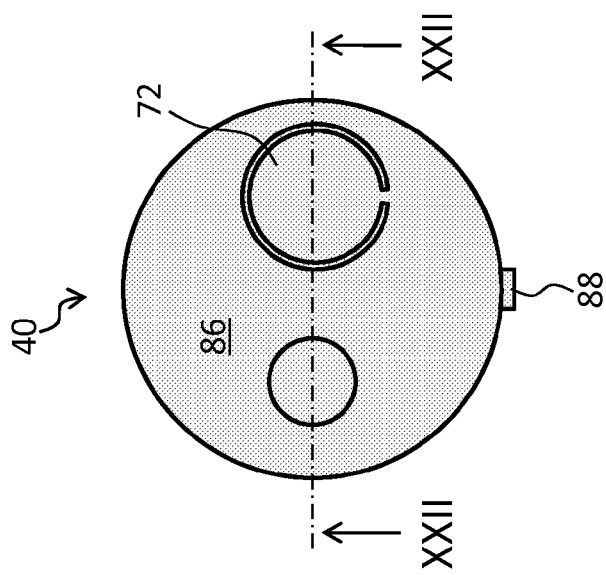
Fig. 21
Fig. 20
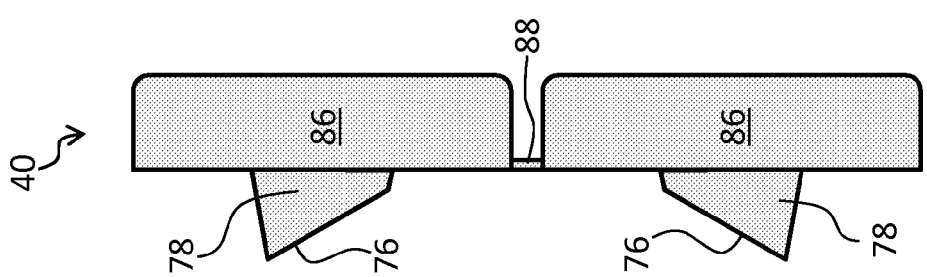
Fig. 19
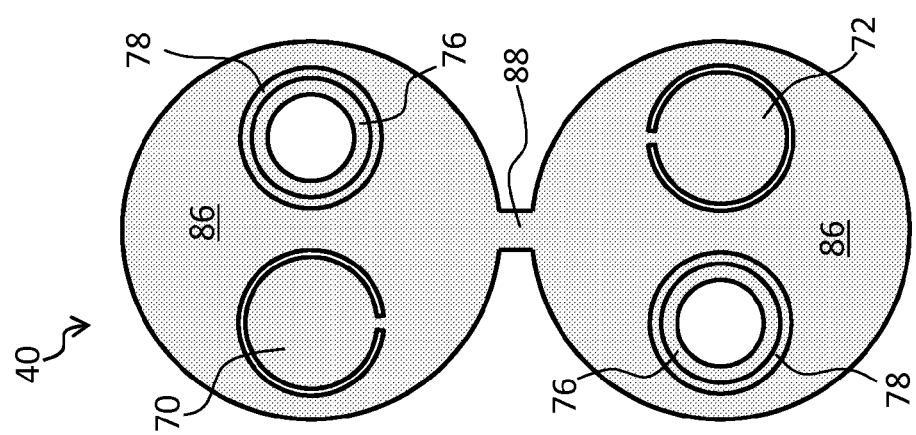
Fig. 18

TUBING SET HAVING A GATE FOR THE CONNECTION OF VIALS

CROSS-REFERENCE TO RELATED APPLICATIONS

This is a national stage of PCT/EP11/053936 filed Mar. 16, 2011 and published in English, which has a priority of Europe no. 10162845.1 filed May 14, 2010, hereby incorporated by reference.

BACKGROUND OF THE INVENTION

1. Field of Invention

The invention concerns a tubing set for a medical liquid delivery device comprising a gate for the connection of vials containing drugs, in particular a tubing set intended to be used with hemodialysis machines. The invention further concerns a method for delivering drugs by means of the tubing set.

2. Description of the Prior Art

Most of the recent hemodialysis machines, are arranged also for carrying out another treatment, called hemofiltration. Hemofiltration is a renal replacement therapy which is used almost exclusively for acute renal failure. During hemofiltration, a patient's blood is passed through a filter where waste products and water are removed. Due to the water removal, a substitution liquid is needed in addition to the blood which is returned to the patient. Hemofiltration is sometimes used in combination with hemodialysis, originating the so called hemodiafiltration treatment.

In view of the above, recent hemodialysis machines, are provided with a specific circuit intended to deliver the substitution liquid.

In the following, for ease of description, reference will be made mainly to hemodialysis, however hemofiltration and hemodiafiltration should also be considered within the scope of the present invention.

In hemodialysis treatments which require an extracorporeal circulation it is often necessary to administer different drugs or therapeutic substances to the patient. The presence of the tubing set advantageously makes it possible to avoid the administering of the drug taking place through puncture carried out directly on the patient himself.

During the hemodialysis treatments it often becomes necessary to administer different drugs or therapeutic substances, like for example iron, heparin, erythropoietin, vitamins and antibiotics. The infusion of such substances in the extracorporeal circuit is currently carried out through conventional syringes or Pre-Filled Syringes (PFS). The substance is drawn from the vial or ampoule in which it is supplied by the producer and is then injected into a special puncturable cap provided along the tubing set. Thus there is a double transfer of the substance: firstly from the vial to the syringe and then from the syringe to the circuit.

Such an operation therefore requires the use of disposable materials, such as the syringe and the respective needle, just to transfer the substance from the vial to the tubing set. Moreover, such operation entails the risk for the service staff to be pricked by the syringe needle or injured by glass fragments originated during snapping off the ampoule neck.

Additionally, glass debris could fall into the ampoule and be delivered in the blood.

Furthermore, each transfer step entails a risk of contamination for the drug to be delivered, e.g. the risk of an accidental multiple use of a syringe.

Finally, some of the quoted substances need to be administered slowly, over a few minutes. From this it can easily be understood how the administering of various substances to more than one patient represents a considerable workload for the nursing staff responsible for the treatment.

WO 87/07159 discloses a medical liquid administration set which is intended for infusions related to an intravenous therapy; such set is not suitable for use in co-operation with a hemodialysis machine.

European patent application No. 09175001.8, filed by the same applicant, discloses a tubing set comprising a vial gate similar to the one set forth in the preamble of claim 1. However, according to that solution, the top end of the vent lumen should be preferably long enough to reach the air reservoir in the upside-down vial. Accordingly, that vial gate is suitable for cooperation with vials of one size only, due to the length of the vent spike. Moreover a long spike entails some problem for its manufacturing and entails some risks during its handling.

SUMMARY OF THE INVENTION

The aim of the present invention is therefore to at least partially solve the drawbacks highlighted in relation to known tubing sets.

A task of the present invention is to avoid the double transfer of the substance.

Another task of the present invention is to make it possible to avoid the use of ampoules, conventional syringes and the respective needles.

Another task of the present invention is to provide a more economic solution if compared to the very expensive Pre-Filled Syringes.

Another task of the present invention is to make it possible to avoid the risks due to transfer steps in the drug delivery, e.g. contamination by glass debris and/or between two drugs.

Another task of the present invention is to allow automated processes for the delivery of any medicament, e.g. to allow slow administering of the substances that require it without needing the active presence of the service staff to do so.

Another task of the present invention is to provide a single vial gate which is suitable for cooperation with vials of different sizes.

The aim and the tasks indicated above are accomplished by a tubing set and by associated methods as described herein.

BRIEF DESCRIPTION OF THE DRAWINGS

The features and the further advantages of the invention shall become clear from the following description of some embodiments, given for indicating and not limiting purposes with reference to the attached drawings, in which:

FIGS. 6 to 8 schematically represent some successive working steps of an assembly according to the invention similar to the one of FIG. 3;

FIGS. 11.a and 11.b represent a sectioned view of a detail similar to the one of FIG. 10 in two different operating conditions;

FIGS. 12.a and 12.b represent a sectioned view of a detail similar to the one of FIG. 10 in two different operating conditions;

FIGS. 16.a and 16.b represent a sectioned view of a detail similar to the one of FIG. 10 in two different operating conditions;

FIGS. 17.a and 17.b represent a sectioned view of a detail similar to the one of FIG. 10 in two different operating conditions;

FIG. 18 represents a plan view of a possible embodiment of the soft element of the vial gate according to the invention, in its disassembled configuration;

FIG. 19 represents a lateral view of the soft element of FIG. 18;

FIG. 20 represents a plan view of a possible embodiment of the soft element of the vial gate according to the invention, in its assembled configuration;

FIG. 21 represents a lateral view of the soft element of FIG. 20;

DETAILED DESCRIPTION OF THE PREFERRED EMBODIMENTS

Figure 1:
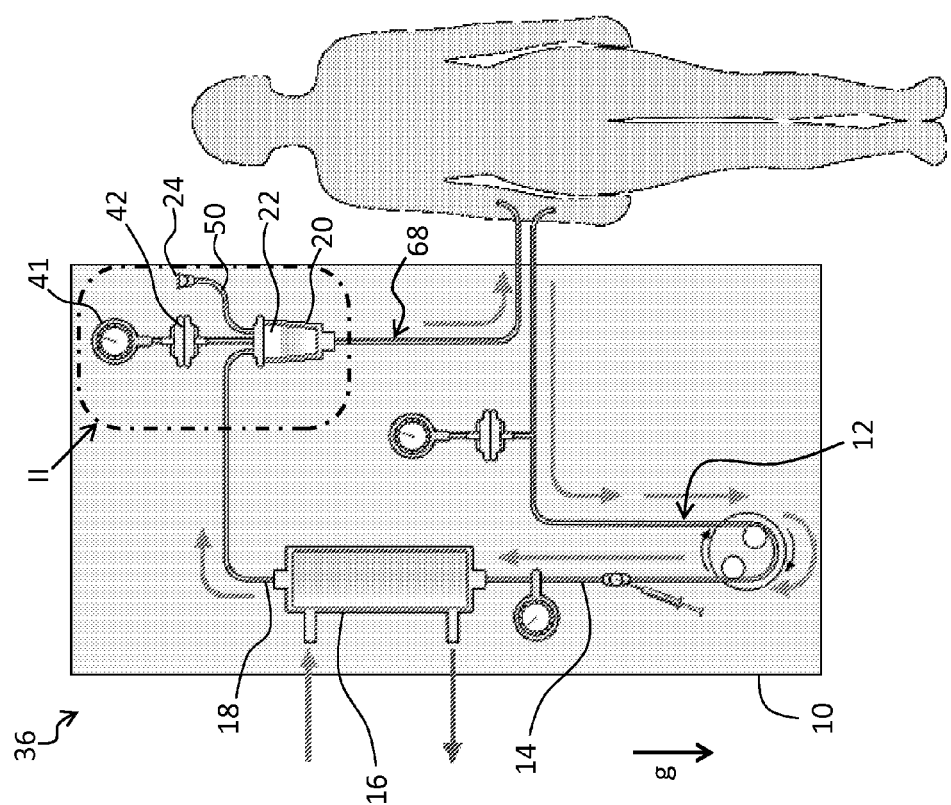
FIG. 1 schematically represents a first tubing set, used in a hemodialysis treatment, according to the invention.
Figure 3:
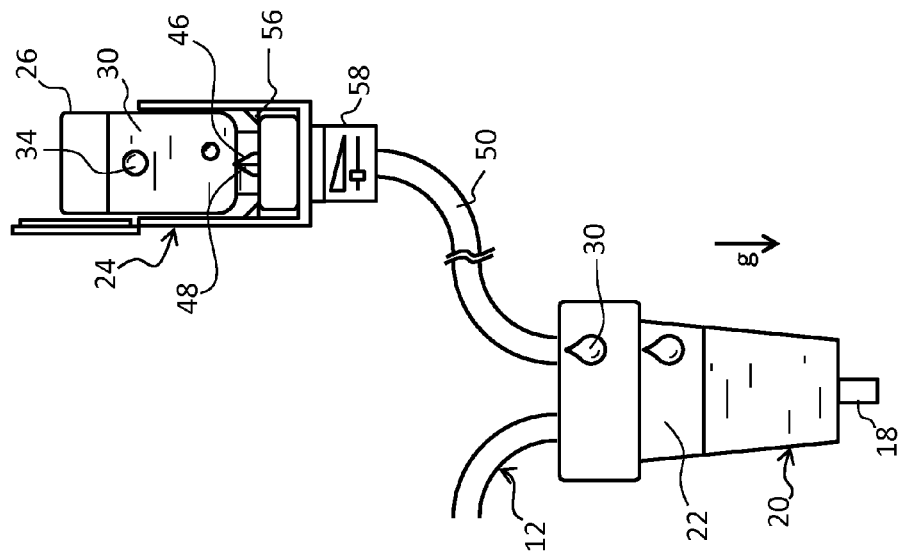
FIG. 3 schematically represents the vial connected on the vial gate of FIG. 2.
Figure 2:
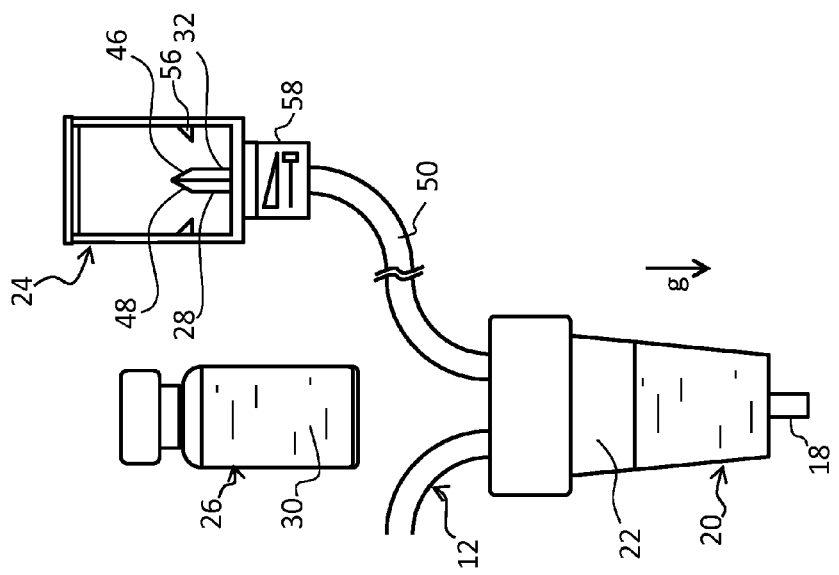
FIG. 2 schematically represents a detail similar to the one indicated with II in FIG. 1 comprising a vial and a vial gate according to the invention.
Figure 5:
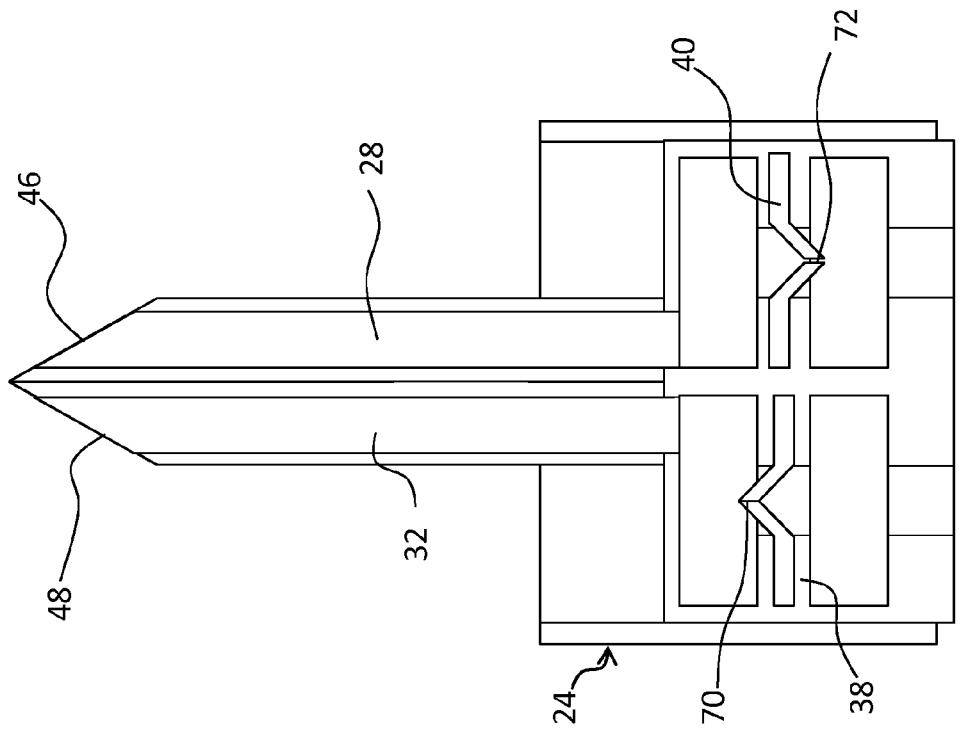
FIG. 5 schematically represents a detail of the vial gate in FIG. 4.
Figure 4:
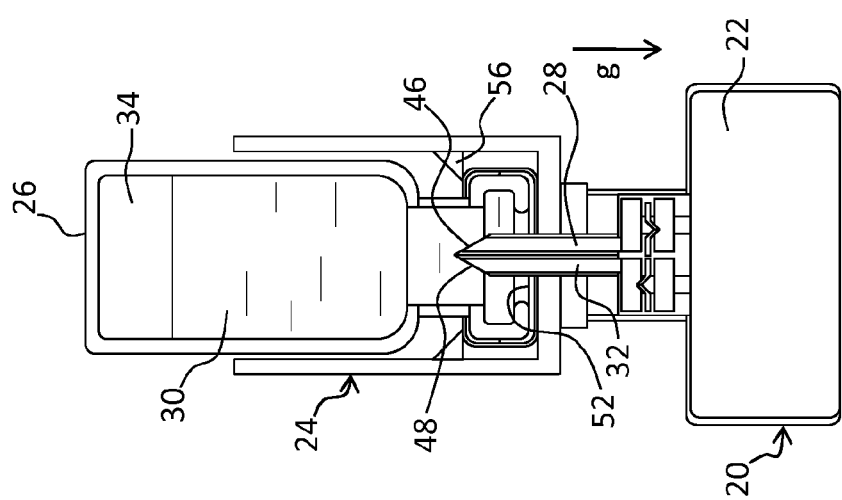
FIG. 4 schematically represents a cross sections of an assembly similar to the one of FIG. 3.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the era from this detailed description.

With specific reference to the enclosed figures, the reference 10 indicates a medical liquid delivery device having a disposable tubing set 12 which comprises:

a delivery tube 68 suitable for supplying a medical liquid or blood to a patient;

a vial gate 24 for the connection of vials 26 containing drugs to be delivered into the medical liquid or blood.

The vial gate 24 comprises a delivery lumen 28, suitable for delivering the drug 30 from the vial 26 to the delivery tube 68; and a vent lumen 32, suitable for providing a replacement fluid 34, 60 from a location inside the tubing set 12 to the inside of the vial 26 in order to replace the delivered drug.

The vial gate 24 according to the invention further comprises at least one one-way valve 70 placed along said vent lumen 32 or said delivery lumen 28.

The expression "one-way valve" is referred to a valve which allows a fluid to flow through it in one direction only, while completely preventing the fluid to flow in the opposite direction. The fluid which is allowed to flow through the valve can be a liquid, a gas, a vapour or even a mixture thereof.

As already reported above, the one-way valve 70 is placed along one of said vent lumen 32 or delivery lumen 28. In the present description the word 'along' is intended to mean that the valve is comprised within the fluid pathway. In other words the one-way valve controls (i.e. allows or prevents) the whole fluid flow enclosed in the lumen along which the valve is placed.

In the description of the invention, reference will be made to the spatial arrangement of the medical liquid delivery device 10 which ensures correct operation thereof. During operation of the invention, in fact, the force of gravity plays a decisive part, especially in some embodiments. In particular, it will be assumed below that the force of gravity is directed as shown by the vector g in some enclosed figures. The vector g therefore defines the vertical direction and is oriented from the top downwards.

According to some embodiments of the invention, the medical liquid delivery device 10 is a hemodialysis machine where a patient's blood is passed through a filter 16 to remove waste products. In such case the tubing set 12, which defines an extra-corporeal circuit 36, further comprises an out-tube 14 for supplying the blood from the patient to a filter 16 of said machine 10. The delivery tube 68 comprises an in-tube 18 for supplying the blood from the filter 16 back to the patient.

According to some embodiments of the invention, the vial gate 24 comprises one one-way valve 70 placed along the vent lumen 32 only. According to other embodiments of the invention, the vial gate 24 comprises one one-way valve 72 placed along the delivery lumen 28 only. According to further embodiments of the invention, the vial gate 24 comprises two one-way valves 70 and 72 placed along the vent lumen 32 and along the delivery lumen 28 respectively.

The presence of the one-way valve 70 allows to exploit the pulsating pressure provided in the delivery tube 68 by the pumps 74. Both peristaltic pumps and membrane pumps, usually used in extra-corporeal circuits and medical liquid delivery, generate a pulsating pressure, i.e. a variable pressure oscillating about a medium value. The value of the pressure in the delivery tube 68 varies along time, alternating peaks (maximum values) and valleys (minimum values) about a medium value. In the diagrams of FIGS. 6 to 8, the value of $P_v$ against time is schematically shown as a very simple pseudo-sinusoid for sake of clarity; however such progress in time actually varies according to different and much more complex periodic functions.

Operation of the vial gate 24 according to the invention is explained in detail below, with specific reference to FIGS. 6 to 8. Such figures show three successive steps of the operation of the invention. In particular, in the lower portion of such figures a diagram is reported representing the progress along time of the venous pressure $P_v$ (i.e. the pressure in the delivery tube 68, e.g. in the in-tube 18). In the upper portion of such figures a section is schematically shown of an assembly formed by a vial gate 24 according to the invention and by a vial 26, at the moment in time indicated on the respective pressure/time diagram.

Such figures schematically show the operation of the invention in its steady state condition, after the initial transient condition. As a matter of fact, the pressure inside the vial 26 is initially equal to the atmospheric pressure, while the pressure inside the drip chamber 20 is higher, usually is 50÷250 mmHg higher. Thus, immediately after the connection of the vial 26 on the vial gate 24, a rapid transient condition occurs during which a first amount of air moves from the drip chamber 20 to the vial 26, balancing the pressure values, and a first amount of drug 30 moves from the vial towards the drip chamber 20. At the end of this rapid transient condition, a steady state operating condition establishes which is disclosed in detail hereinafter.

As shown by the diagram of FIG. 6, at time $t_0$ pressure $P_v$ reaches its maximum value. In such condition the pressure difference between the drip chamber 20 and the vial 26 pushes air 34 of the air buffer 22. Accordingly air 34 flows along the vent lumen 32, up to the vial 26. In particular, the presence of the one-way valves 70 and 72 determines in a definite manner that air 34 is pushed along the vent lumen 32 rather than along the delivery lumen 28.

Successively, as shown by the diagram of FIG. 7, at time $t_1$ pressure $P_v$ reaches its minimum value. In such condition the pressure difference between the drip chamber 20 and the vial 26 sucks the drug 30 from the vial 26. Accordingly, drug 30 flows along delivery lumen 28, down to the drip chamber 20. In particular, the presence of the one-way valves 70 and 72 determines in a definite manner that drug 30 is sucked along the delivery lumen 28 rather than along the vent lumen 32.

FIG. 8 shows, at time $t_2$, a condition similar to the one of FIG. 6, wherein pressure $P_v$ reaches again its maximum value and air 34 is pushed again along the vent lumen 32. Then, operation of the invention cyclically repeats the above steps.

As can be noticed from the above description, the vial gate 24 according to the invention allows, during the pressure pulsation, to dynamically maintain an equilibrium between the pressure inside the drip chamber 20 and the pressure inside the vial 26. At the same time, the presence of the one-way valve(s) 70 (and 72) forces the flowing fluids (air 34 and drug 30) to move along a specific way (vent lumen 32 and delivery lumen 28 respectively) between the drip chamber 20 and the vial 26. In such a manner delivery of the drug 30 is obtained.

In order to let the invention work properly, it is advisable that the opening pressure of the valves 70 and/or 72 is lower than the pressure difference between the peaks and the valleys of the pulsating pressure. Thus, the opening pressure of the at least one valve 70 and/or 72 should be lower than 40 mmHg, preferably comprised between 0.1 mmHg and 25 mmHg, more preferably comprised between 1 mmHg and 10 mmHg.

Some test have been carried out by the applicant for delivering a drug 30 from a vial 26 using a tubing set 12 according to the invention. The pressure generated by a peristaltic pump oscillated between 120 mmHg (maximum value) and 80 mmHg (minimum value), with a medium value of 100 mmHg.

According to a first test, one one-way valve 70 was used, along the vent lumen 32 only. The opening pressure of the one-way valve 70 was about 5 mmHg. With a flow rate in the delivery tube 68 of 200 ml/min, the delivery of 2.5 ml of drug 30 took a time comprised in the range between 73 seconds and 134 seconds, depending on the different flow resistance in the respective circuits (e.g due to the setting of the flow regulator 58, described in detail below).

According to a second test, two identical one-way valves 70 and 72 were used, both along the vent lumen 32 and along the delivery lumen 28. With a flow rate in the delivery tube 68 of 200 ml/min, the delivery of 2.5 ml of drug 30 took a time of 26 sec. Of course a longer delivery time can be obtained by means of different settings for the flow regulator 58.

FIGS. 4 to 8 and 11 schematically show the one-way valves in the form of duck-bill valves. An actual embodiment of such kind of valve, widely used in medical devices, is disclosed for example in EP 0 637 971. According to FIGS. 4-5 and 11, a rigid element 38, which defines the structure of the vial gate 24, encloses a soft element 40, which defines the duck-bill valves 70 and 72.

Figure 10:
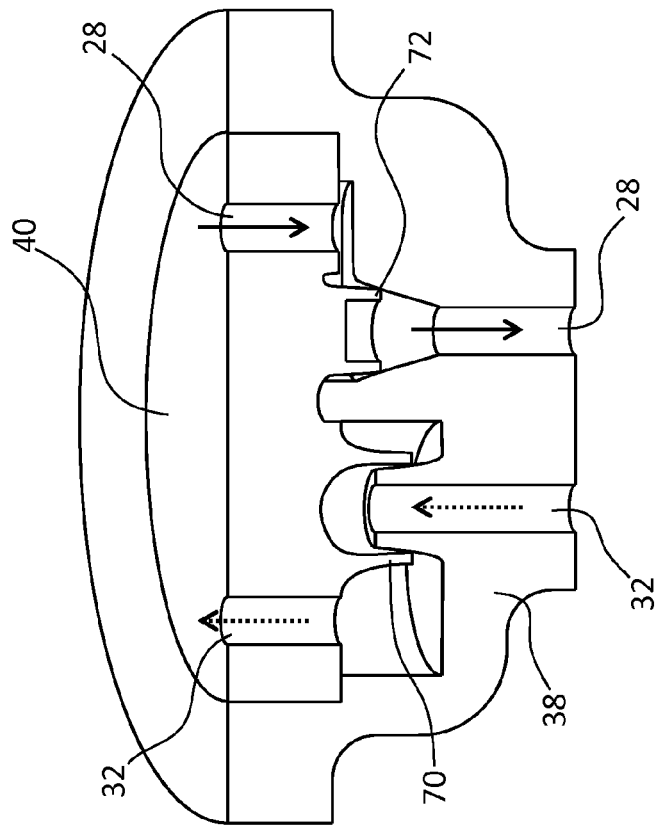
FIG. 10 represents a partly sectioned view of a detail of a vial gate according to the invention.
Figure 9:
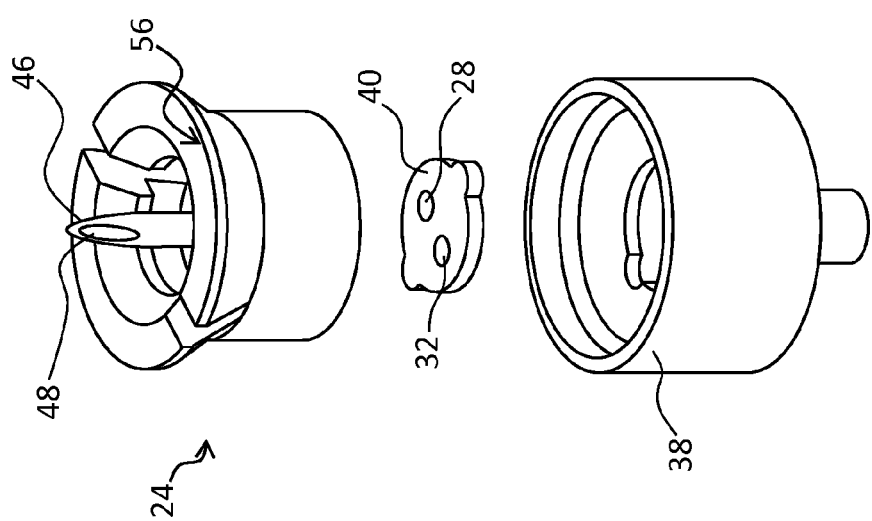
FIG. 9 represents an exploded view of a vial gate according to the invention.

FIG. 10 shows another embodiment of the one-way valves 70 and 72, a so-called lip valve. In such embodiment a rigid element 38 of the interior vial gate is covered by a soft element 40. The soft element 40 forms lips over the channels formed by the rigid element 38. Each soft lip may be easily loosened from the rigid channel when pressure is exerted in one direction, allowing a fluid to flow. On the contrary, when the pressure is exerted in the other direction, the soft lip is pressed tight onto the rigid channel stopping the fluid flow.

FIGS. 12.a and 12.b show a further embodiment of the one-way valves 70 and 72, a so-called flap valve. Also in such embodiment a rigid element 38 of the interior vial gate is covered by a soft element 40. The soft element 40 forms flaps resting over respective rims formed along the channels. Each flap may be easily loosened from the rim when pressure is exerted in one direction, allowing a fluid to flow. On the contrary, when the pressure is exerted in the other direction, the flap is pressed tight onto the rim stopping the fluid flow. According to some embodiments of the flap valve, even in case of no back pressure, the flaps rest on their rims, thus maintaining the valve in its closed configuration.

For example, in the further embodiment of FIG. 16, the flap of each valve is not strictly perpendicular to the axis of the flow channel; on the contrary, the flap is slightly angled and its loose end rests on a raised rim 76 when the valve is in its closed configuration. In other words, the raised rim 76 obtained by means of a angle-cut protruding cone 78 (see also FIG. 19 for a disassembled view) obtains the effect of introducing a pre-load for the valve flaps. This design ensures a more reliable closure of the valve 70 when no flow pressure is exerted.

According to a further embodiment shown in FIG. 17, the opening movement of at least one flap valve is limited by a blocking element 84. The limitation of the opening of the valve may serve as a flow regulation means as will be explained below.

In a further embodiment of the vial gate 24 (not shown), the one-way valve 70 on the vent lumen 32 comprises a porous vented septum. In particular, such septum comprises a hydrophobic membrane which is gas-permeable and liquid-tight. According to such embodiment, the membrane lets air flow along the vent lumen 32 when pressure $P_v$ is at its maximum value. On the contrary, the membrane prevents drug 30 to flow along the vent lumen 32, thus forcing it to flow along the delivery lumen 28 when pressure $P_v$ is at its minimum value. Hydrophobic membranes are not disclosed in detail since they are well known in the art.

According to the above description, the vial gate 24 comprises both rigid elements 38 and soft elements 40. The vial gate 24 can be advantageously manufactured, in a manner known per se, by means of the two component injection moulding technique.

The rigid elements 38 are made of a rigid material, preferably a rigid polymer. Polymers which are suitable for such use are for example: polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS), and copolyesters.

The soft elements 40 are made of an elastic material, preferably an elastomer. Elastomers which are suitable for such use are for example: Silicone Rubber, Styrene-Ethylene-Butylene-Styrene (SEBS), Styrene-Ethylene-Propylene-Styrene (SEPS), Styrene-Isoprene-Styrene (SIS), Styrene-Butadiene-Styrene (SBS), Poly-Urethane (PU), polyisoprene, ThermoPlastic Elastomer (TPE), Natural Rubber (NR) and latex.

Figure 22:
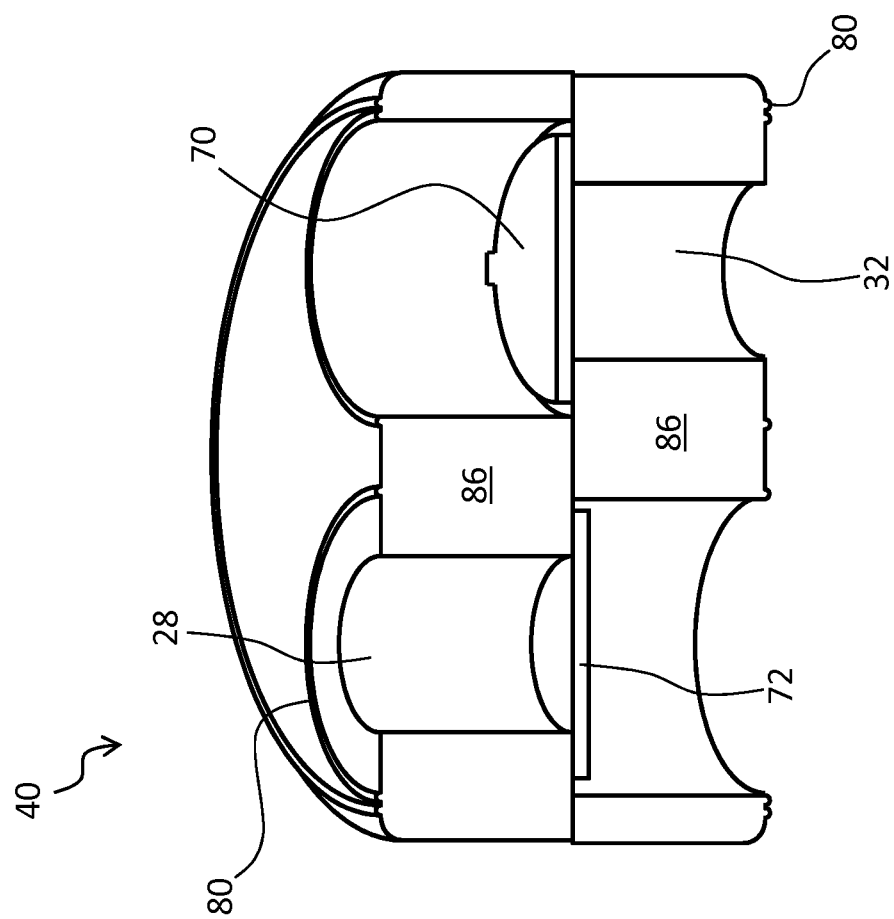
FIG. 22 represents a sectioned view along plane XXII of FIG. 20.

According to one possible embodiment, the soft element 40 is obtained from two discs 86 pressed onto each other. Preferably both discs are identical. This solution, shown in FIGS. 18 to 22, permits to easily obtain an effective soft element 40 comprising miniature scale valves 70, 72 and gasket portions 80 (see FIG. 22). The entire soft element 40 may be made from one of the flexible materials listed above, preferably silicone rubber. In its disassembled form, the soft body 40 is comprised of two separate discs 86 or even preferably of a single 8-shaped element (see FIG. 18). In order to obtain the soft element 40, the discs 86 are superimposed one other, preferably by folding over the flexible linking bar 88 of the 8-shaped element (see FIGS. 20 and 21). As can be appreciated, this design permits to easily obtain miniature scale flap valves 70 and 72. As a matter of fact, for each valve, the flap and the rim are separately obtained from two different discs 86. Moreover, the raised gasket portions 80 may serve as liquid-tight seals between the rotatable parts of the vial gate 24, both in the open and in the closed configuration.

According to some embodiment of the invention, the vial gate 24 comprises means 56 for ensuring a safe connection of the vial 26. Such means, which are not shown in detail in the attached figures, are preferably designed to ensure a tight closure of the extra-corporeal circuit 36 in absence of any vial 26. Moreover, the safe connection means 56 are preferably so arranged that the fluid connection can be opened only when a vial 26 is properly placed on the vial gate 24 and, respectively, the vial 26 can be removed only when the fluid connection is closed.

Some safe connection means 56 suitable for such use are known in the art. Italian Patent Application number TO2009A000455 in the name of Borla Industrie S.p.A. discloses a device which, among some other technical features, comprises safe connection means which are suitable for the present use.

According to some embodiments of the invention, the vial gate 24 further comprises a flow regulator 58 for adjusting the delivery rate of the drug 30. The flow regulators 58 are well known in the art. They can comprise for example an adjustable flow restrictor suitable for adjustably obstructing the inner cross section of the delivery lumen 28. Otherwise, the flow regulator 58 can comprise a fixed flow restrictor, for example a calibrate narrowing along the delivery lumen 28.

Figure 24:
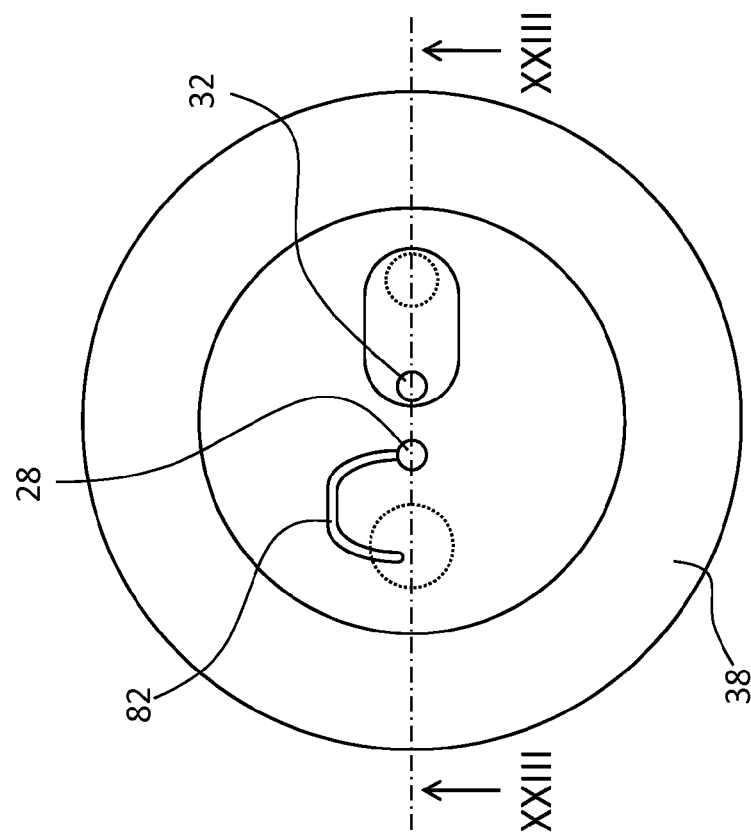
FIG. 24 represent a plan view of the rigid element of FIG. 23.
Figure 23:
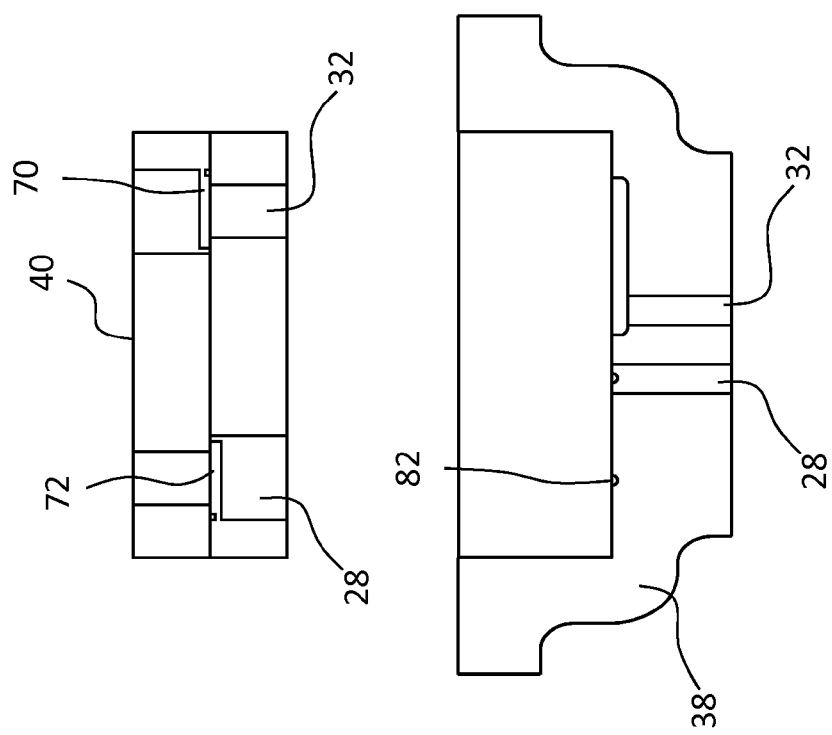
FIG. 23 represents an exploded view of a detail of a vial gate similar to the one of FIG. 12.

An example of a possible narrowing along the delivery lumen 28 is shown in FIGS. 23 and 24. In this embodiment, the narrowing is obtained by means of a capillary 82 immediately downstream of the delivery valve 72 along the delivery lumen 28. According to the embodiment of FIGS. 23 and 24, the capillary 82 is engraved in the upper wall of the rigid element 38, however other possible solutions are possible, e.g. to engrave the capillary in the lower wall of the soft element 40. According to such solution, the capillary 82 has preferably a semicircular cross section, even if other cross sections may be provided. The cross section of the capillary 82 has preferably a diameter of less than 2 mm, more preferably less than 1 mm; the length of the capillary 82 is preferably more than 5 mm.

As already described before, according to some embodiments of the invention, the flap valve comprises a blocking element 84 suitable for limiting the opening movement of the flap. Such limitation obtains the effect of limiting the open section of the lumen 28 or 32 thus limiting the amount of fluid which can pass through the lumen during each pulse. This solution may serve also as a flow regulation means.

All the above described flow regulation means (i.e. the adjustable flow restrictor, the calibrate narrowing like the capillary, the blocking element for the valve flap) can be used either in combination or separately.

With reference to FIG. 1, a tubing set 12 according to the invention is described which is associated with a hemodialysis machine 10 and which defines an extra-corporeal circuit 36.

The tubing set 12 mainly comprises an out-tube 14 and an in-tube 18. Along said tubing set 12 at least a drip chamber 20 is provided. The drip chamber 20 is adapted to let the blood drip through an air buffer 22 in order to remove from the blood any possible gas bubble. According to some embodiments, e.g. those shown in FIGS. 1 to 8, the vial gate 24 is connected to the drip chamber 20. According to such embodiments, the delivery lumen 28 of the vial gate 24 is preferably arranged so as to deliver the drug 30 from the vial 26 to the drip chamber 20. According to some embodiments, the vent lumen 32 preferably connects the vial 26 and the air buffer 22 in the drip chamber 20, thus providing air 34 inside the vial 26 in order to replace the delivered drug.

In the enclosed figures and in the following description, the drip chamber 20 is considered to be placed along the in-tube 18 which supplies the filtered blood back to the patient. The drip chamber 20 is preferably placed along the in-tube 18, thus avoiding the drug 30 to pass through the filter 16, by which it could be easily removed and disposed of together with the waste products. However, nothing would substantially change by placing the drip chamber 20 along the out-tube 14 or another auxiliary tube of the circuit 36.

According to some embodiments, the vial gate 24 is directly connected to the drip chamber 20. In particular, the vent lumen 32 puts in communication the interior of the vial 26 with the air buffer 22; the delivery lumen 28 puts in communication the interior of the vial 26 with the drip chamber 20.

Accordingly, the drug 30 is drawn down along the delivery lumen 28 and air 34 is pushed up along the vent lumen 32 by pulsating pressure. The volume of the delivered drug 30 is thus automatically compensated by an equal volume of air 34, accordingly the pressure inside the vial 26 is promptly equalized to the pressure inside the drip chamber 20.

The drip chamber 20 provides an air buffer 22 for receiving and stopping any possible gas bubble contained in the liquid to be delivered, e.g. blood. The air buffer 22 is also connected to a pressure transducer 41 by means of a proper pressure conduit. Such pressure transducer 41 is intended to constantly provide a measurement of the pressure inside the drip chamber 20. The pressure transducer is protected by a transducer protector 42 placed along the pressure conduit. The transducer protector 42 comprises a hydrophobic semipermeable membrane which is gas-permeable and liquid-tight. This arrangement, known per se, is intended to avoid any possible blood contamination of the non-disposable portion of the extra-corporeal circuit 36. At the same time it allows the air to freely and safely move along the pressure conduit so as to instantly provide the pressure value from the drip chamber 20 to the pressure transducer 41.

The proper operation of the pressure transducer 41 and the safe removal of the gas bubbles from the liquid flow strictly depend on the presence of the air buffer 22 inside the drip chamber 20. Since the air buffer 22 is crucial, an air pump is provided on the machine 10 to restore the correct air amount in the drip chamber 20, if needed. In practice, in a manner known per se, if the liquid level becomes too high (i.e. the air buffer 22 is reduced), air is pumped in the drip chamber so as to restore the correct blood level.

In the vial gate 24 according to the invention, the top portion of the delivery lumen 28 can be identical to the top portion of the vent lumen 32. Due to the at least one one-way valve 70 and/or 72, no difference between the two top portions is needed to facilitate the drug 30 to flow downward into the delivery lumen 28 rather than into the vent lumen 32. At the same time air 34 is allowed to flow upward along the vent lumen 32, without any conflict occurring with the downflowing drug 30. Reference is made in the following to FIGS. 2 to 9, where both the top portions of the delivery lumen 28 and of the vent lumen 32 comprise a hollow spike.

According to the above embodiments, the delivery of the drug 30 involve the air 34 to be sucked from the air buffer 22 of the drip chamber 20 into the liquid drug 30 so as to form bubbles which rise up to the top of the vial 26 (see FIGS. 6 and 8)

In all the embodiments, in their proper use configuration, the vial gate 24 is preferably located above the drip chamber 20. According to some embodiments (e.g. those shown in FIGS. 4 to 8) the vial gate 24 is directly mounted on the top wall of the drip chamber 20. According to some other embodiments (e.g. that shown in FIGS. 1 to 3) the vial gate 24 is mounted in a remote position with respect to the drip chamber 20 and is connected thereto by means of a double tube 50. Any of such different configurations may be advantageously adopted in order to deal with specific issues deriving from the overall arrangement of the dialysis machine 10.

Figure 13:
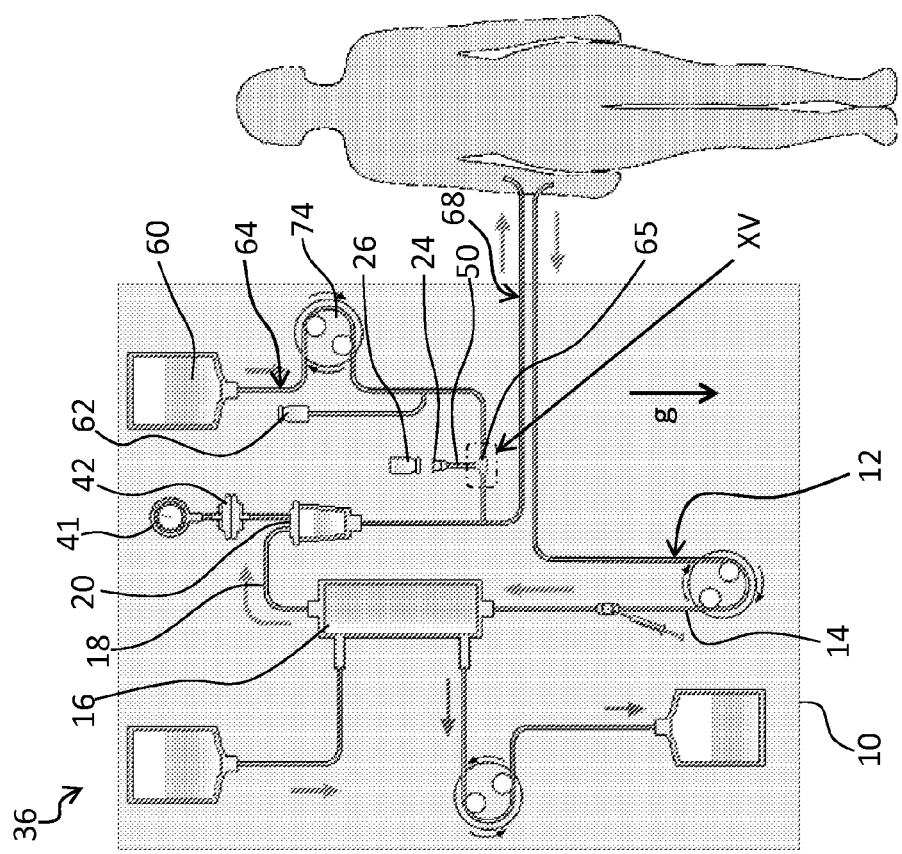
FIG. 13 schematically represents a second tubing set, used in a hemodiafiltration treatment, according to the invention.
Figure 15:
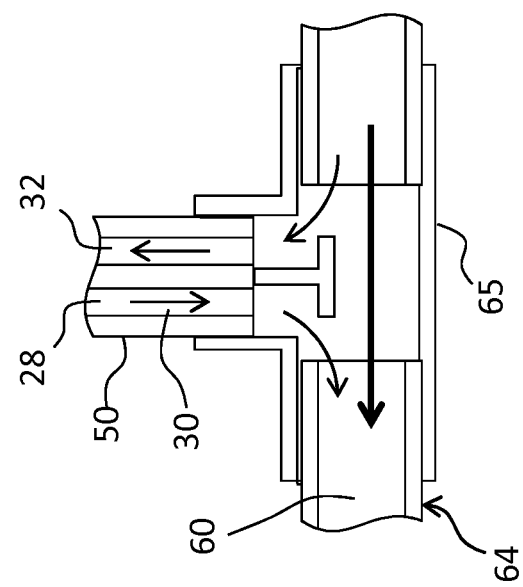
FIG. 15 schematically represents a sectioned view of the detail indicated with XV in FIGS. 13 and 14.
Figure 14:
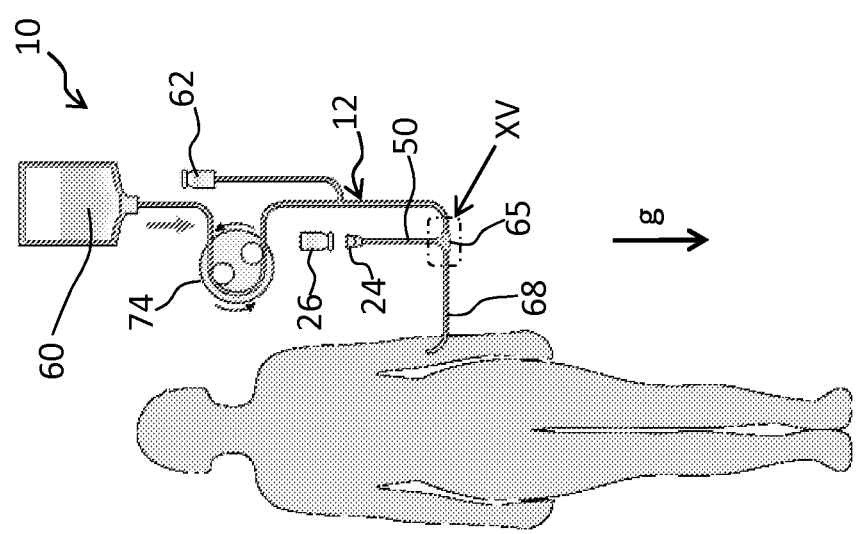
FIG. 14 schematically represents a third tubing set, used in an infusion treatment, according to the invention.

A second type of embodiments of the tubing set 12 according to the invention will be now disclosed in detail, with further reference to FIGS. 13 to 15. Such embodiments of the tubing set 12 comprise a solution line 64 intended to deliver a physiological liquid or solution 60 to the patient. The solution line 64 may be either an infusion line for intravenous therapies, e.g. delivering a saline solution, or a substitution line needed on some hemodialysis machines 10 as described in detail below.

Most of the recent hemodialysis machines 10 are designed according to the scheme of FIG. 13 rather than those of FIG. 1. Such machines 10 are intended to perform also hemofiltration and/or hemodiafiltration treatments. Such treatments imply the removal of some waste water from the blood and, accordingly, they need also to compensate the removal by means of the addition of medical solution, i.e. the so called substitution liquid 60. Thus, hemofiltration machines comprise also a solution line 64.

In the above cases, the vial gate 24 may be advantageously connected to the solution line 64 rather than to the drip chamber 20.

According to such embodiments, the delivery lumen 28 of the vial gate 24 is arranged so as to deliver the drug 30 from the vial 26 to the line 64. Moreover, the vent lumen 32 also connects the vial 26 and the solution line 64, thus providing solution 60 inside the vial 26 in order to replace the delivered drug 30. A possible connection of the vial gate 24 to the solution line 64 comprises a double tube 50 and a T-shaped connector 65 similar to the one schematically shown in FIG. 14. According to such connection, both the delivery lumen 28 and the vent lumen 32 are connected to the solution line 64 where the solution 60 flows. Preferably, the intake of the vent lumen 32 is placed upstream the outlet of the delivery lumen 28.

As the skilled person may easily understand, the operation of this embodiments is perfectly analogous to the one described above with reference to FIGS. 6 to 8. In particular, the presence of the at least one one-way valve 70 allows to exploit the pulsating pressure $P_s$ provided in the solution line 64 by the pump 74.

At time $t_0$ pressure $P_s$ reaches its maximum value, similarly to what has been described above with respect to FIG. 6. In such condition the pressure difference between the solution line 64 and the vial 26 pushes solution 60. Accordingly solution 60 flows along the vent lumen 32, up to the vial 26. The at least one-way valve 70 determines in a definite manner that solution 60 is pushed along the vent lumen 32 rather than along the delivery lumen 28.

Successively, at time $t_1$ pressure $P_s$ reaches its minimum value, similarly to what has been described above with respect to FIG. 7. In such condition the pressure difference between the solution line 64 and the vial 26 sucks drug 30. Accordingly, drug 30 flows along the delivery lumen 2S, down to the solution line 64. The at least one-way valve 70 determines in a definite manner that the drug 30 is sucked along the delivery lumen 28 rather than along the vent lumen 32.

Successively, at time $t_2$ pressure $P_s$ reaches again its maximum value, similarly to what has been described above with respect to FIG. 8. The solution 60 is pushed again along the vent lumen 32. Then, operation of the invention cyclically repeats the above steps.

It has been observed by the applicant that the flow rate of the solution 60 in the main substitution line of a hemodialysis machine, which is typically quite high, could result in a too fast flushing of the drug 30 from the vial 26.

If a too fast flushing of the drug 30 is to be avoided, one or more of the following expedients can be adopted.

As a first expedient, a flow regulator 58 can be placed along the delivery lumen 28. As a second expedient, the T-shaped connector 65 can be placed on a by-pass line (not shown) having a smaller diameter and a smaller flow rate than the main solution line 64. As a third expedient, both the flow regulator 58 and the by-pass line can be adopted together.

As can be noticed from the above description, the vial gate 24 according to the invention allows, during the pressure pulsation, to dynamically maintain an equilibrium between the pressure inside the solution line 64 and the pressure inside the vial 26. At the same time, the presence of the at least one one-way valve 70 forces the flowing fluids (solution liquid 60 and drug 30) to move along a specific way (vent lumen 32 and delivery lumen 28 respectively) between the solution line 64 and the vial 26. In such a manner delivery of the drug 30 is obtained.

According to the previously disclosed embodiments, wherein the vent lumen 32 connects the vial 26 with the air buffer 22 in the drip chamber 20, air 34 progressively replaces the drug 30 inside the vial 26. At the end of the delivery, there is no drug 30 in the vial 26 which is completely empty. According to the embodiments disclosed above, wherein the vent lumen 32 connects the vial 26 with the solution line 64, solution 60 progressively dilutes the drug 30 inside the vial 26. At the end of the delivery, there is almost no drug 30 in the vial 26 which contains substantially solution 60 only.

The above embodiments of the invention, wherein the vial gate 24 is placed along the solution line 64, are suitable also for delivering drugs in powder or lyophilized form. According to such embodiments, the solution 60 progressively enters the vial 26 and can either dilute a liquid drug 30 or dissolve a powdered or lyophilized drug 30. In the latter case the solution 60 is used as a carrier agent.

According to some embodiments (not shown) the vial gate 24 is directly mounted on the solution line 64. According to some other embodiments (see for example FIG. 13) the vial gate 24 is mounted in a remote position with respect to the solution line 64 and is connected thereto by means of a double tube 50. Any of such different configurations may be advantageously adopted in order to deal with specific issues deriving from the overall arrangement of the dialysis machine 10.

In all the embodiments, the opening at the top end 48 of the delivery lumen 28 is advantageously placed so as to be, when the vial 26 is properly connected to the vial gate 24, as close as possible to the puncturable membrane 52 of the vial 26. An opening of the delivery lumen which is very close to the membrane 52 allows a very effective emptying of the vial 26, i.e. allows a complete delivery of the drug 30.

The vial gate 24 is intended as a delivery point for several different drugs. Accordingly, when the delivery of a first drug comes to an end, the related first vial 26 can be removed and replaced by a second vial 26 containing a second drug. If incompatibility issues occur between the first and the second drug, one or more of the following expedients can be adopted.

As a first expedient, the delivery lumen 28, intended to successively contain the flows of the two incompatible drugs, may be advantageously designed so as to be as short as possible. In such a way, the remainder droplets of the first drug, which will be mixed with the flow of the second drug, are minimized. This solution can be obtained for example by mounting the vial gate 24 directly on the top wall of the drip chamber 20 (see FIGS. 4 to 8) or directly on the solution line 64 (not shown).

As a second expedient, the delivery lumen 28 may advantageously comprise means suitable for minimizing the adhesion of the drug droplets. Such means may in turn comprise an inner layer having low adhesion properties. A lumen with such an inner layer may be manufactured by co-extrusion, polymer grafting or coating with a low adhesion material known in the art. For example one solution is to have a surface obtained from a very hydrophobic material, for example from Poly-TetraFluoroEthylene (PTFE) or of other similar materials. Another solution is to attach a hydrophilic hydrogel by coating or grafting and thereby increasing the fluid flow on the surface by enhancing the wettability. This solution and some related methods for providing a hydrogel coating on a polymer substrate are described for example in U.S. Pat. No. 7,572,489.

As a third expedient, a washing solution may be used for washing the delivery lumen 28 so as to remove the remainder droplets of the first drug before the delivery of the second drug. Such washing solution may be for example supplied by means of a simple vial 26. Otherwise the washing solution may be supplied by the solution line 64. In the latter case, the solution line 64 may advantageously comprise a fake vial 62, fed by the solution 60 flowing in the circuit 64, and suitable for being connected to the vial gate 24 exactly like a common vial 26.

The invention also relates to a method for delivering a drug 30 in an extra-corporeal circuit 36 of a medical device 10. The method comprises the steps of:
  providing the medical device 10 with a tubing set 12 according to the invention;
  operating a pump 74 so as to originate a pulsating pressure in the delivery tube 68; and
  connecting a vial 26 to the vial gate 24, so as to put in communication the interior of the vial 26 both with a delivery lumen 28 and with a vent lumen 32, the delivery lumen being suitable for delivering the drug 30 to the delivery tube 68, and the vent lumen 32 being suitable for providing a replacement fluid 34, 60 inside the vial 26 in order to replace the delivered drug 30.

According to some general embodiments of the invention, the method further comprises one or more of the following steps:
  providing a hemodialysis machine, as medical device 10, for carrying out a hemodialysis treatment of a patient's blood;
  opening the fluid connection between the vial 26 and the extra-corporeal circuit 36 by means of the safe connection means 56;
  adjusting the delivery rate of the drug 30 by means of the flow regulator 58.
  closing the fluid connection between the vial 26 and the delivery tube 68 by means of the safe connection means 56 and, subsequently, removing the vial 26 from the vial gate 24.

More generally, the invention relates also to a method for delivering an additive in a circuit of a device. The method comprises the steps of:
  providing the device with a tubing set 12 according to the invention;
  operating a pump 74 so as to originate a pulsating pressure in the delivery tube 68; and
  connecting a vial 26 to the vial gate 24, so as to put in communication the interior of the vial 26 both with a delivery lumen 28 and with a vent lumen 32, the delivery lumen being suitable for delivering the additive to the delivery tube 68, and the vent lumen 32 being suitable for providing a replacement fluid 34, 60 inside the vial 26 in order to replace the delivered additive 30.

According to some embodiments of the invention, the method further comprises one or more of the following steps:
  providing a treatment machine, as device, for carrying out a treatment of a liquid;
  opening the fluid connection between the vial 26 and the circuit by means of the safe connection means 56;
  adjusting the delivery rate of the additive by means of the flow regulator 58;
  closing the fluid connection between the vial 26 and the delivery tube 68 by means of the safe connection means 56 and, subsequently, removing the vial 26 from the vial gate 24.

As the skilled person can appreciate, the tubing set 12 according to the invention has no opening towards the environment. In particular, the vent lumen 32 is intended to supply a replacement fluid (air 34 or solution 60) inside the vial 26 by drawing it from another location inside the overall tubing set 12. Such location can be the drip chamber 20, where air 34 is drawn, or the solution line 64, where solution 60 is drawn. Such arrangement permits to exploit the pulsating pressure and also avoids any contaminating agent to enter the delivery tube 68 from outside.

From the above described operation of the invention, the skilled person will easily appreciate that the drug delivery is synchronized with the pump rotation. Accordingly, the dilution of the drug 30 delivered in the delivery tube 68 is almost constant over different working conditions, once the flow regulator 58 is set. In particular, the pressure conditions in the drip chamber 20 being the same, the dilution of the drug 30 does not depend on the flow rate.

In view of the above description, the skilled person will easily appreciate that the present invention overcomes most of the drawbacks pointed out with respect to the prior art. In particular, the present invention avoids the double transfer of the drug, from the vial to the syringe first and then from the syringe to the extra-corporeal circuit.

Moreover the present invention avoids the use of some disposable items, i.e. the pre-filled syringes or the conventional syringes and the respective needles.

Furthermore, the present invention allows slow administering of the drugs that require it, without needing the active presence of the service staff to do so.

Finally, the present invention provides a single vial gate which is suitable for cooperation with vials of different sizes.

The person skilled in the art can bring modifications and/or replacements of described element with equivalent elements to the embodiments of the tubing set and of the vial gate according to the invention described above, in order to satisfy specific requirements, without for this reason departing from the scope of the attached claims.

What is claimed is:

1. A tubing set, suitable for use in co-operation with a medical liquid delivery device, comprising:
    a delivery tube configured for supplying a medical liquid or blood to a patient;
    a vial gate for connection of vials containing drugs to be delivered into the medical liquid or blood, the vial gate including a first lumen, configured for delivering the drug from the vial to the delivery tube, and a second lumen, configured to provide a replacement fluid that originates from a location inside the tubing set to the inside of the vial in order to replace the delivered drug, the vial gate including a one-way valve located along the first lumen or the second lumen, and an element to provide for a secure connection of the vial, the element being configured to ensure a tight closure of an extra-corporeal circuit in the absence of any vial, arranged so that the connection is openable only when a vial is properly placed on the vial gate, and arranged so that the vial is removable only when the connection is closed.

2. The tubing set according to claim 1, configured for use in co-operation with a hemodialysis machine, defining an extra-corporeal circuit and further comprising an out-tube for supplying the blood from the patient to a filter of said machine, said delivery tube including an in-tube for supplying the blood from the filter back to the patient.

3. The tubing set according to claim 1, wherein the vial gate includes a one one-way valve placed along the first lumen.

4. The tubing set according to claim 1, wherein the vial gate includes a one one-way valve placed along the second lumen.

5. The tubing set according to claim 1, configured for being connected to a pump providing a pulsating pressure in said tubing set, said pulsating pressure varying along time alternating maximum values and minimum values about a medium value, and wherein an opening pressure of the one-way valve is lower than a pressure difference between the maximum values and the minimum values of the pulsating pressure.

6. The tubing set according to claim 1, wherein the opening pressure of the one-way valve is lower than 40 mmHg.

7. The tubing set according to claim 1, wherein said one-way is selected from the group consisting of duck-bill valves, lip valves, flap valves, and porous vented septa.

8. The tubing set-according to claim 1, wherein said one-way valve is a flap valve wherein a flap thereof, when the valve is closed, rests on a raised rim to provide an effect of introducing a pre-load for the valve flap.

9. The tubing set according to claim 1, wherein said one-way valve is a flap valve that includes a blocking element configured to limit an opening movement of a valve flap thereof.

10. The tubing set according to claim 1, wherein the vial gate further comprises a flow regulator for adjusting a delivery rate of the drug along the first lumen.

11. The tubing set according to claim 10, wherein the flow regulator includes a narrowing along the first lumen.

12. The tubing set according to claim 11, wherein the narrowing along the first lumen includes a capillary.

13. The tubing set according to claim 1, further comprising a drip chamber along said tubing set, the vial gate being connected to the drip chamber.

14. The tubing set according to claim 13, wherein the first lumen of the vial gate is arranged so as to deliver the drug from the vial to the drip chamber.

15. The tubing set according to claim 13, wherein the second lumen connects the vial and an air buffer in the drip chamber so as to provide air inside the vial as a replacement fluid.

16. The tubing set according to claim 1, further comprising a solution line configured to supply a solution for infusion treatments or for hemofiltration/hemodiafiltration treatments, the vial gate being connected to the solution line.

17. The tubing set according to claim 16, wherein the first lumen of the vial gate is arranged so as to deliver the drug from the vial to the solution line.

18. The tubing set according to claim 16, wherein the second lumen connects the vial and the solution line so as to provide a substitution liquid inside the vial as a replacement fluid.

19. The tubing set according to claim 1, wherein the vial gate includes a rigid element defining a structure of the vial gate and a soft element defining the one-way valve, wherein the soft element is configured as two discs pressed onto each other.

20. The tubing set according to claim 19, wherein the valve includes a flap and a rim, the flap and the rim of the valve being separately obtained from two different discs.

21. The tubing set according to claim 6, wherein the opening pressure of the one-way valve is between 0.1 mmHg and 25 mmHg.

22. The tubing set according to claim 21, wherein the opening pressure of the one-way valve is between 1 mmHg and 10 mmHg.

23. A method of delivering a drug in an infusion line, comprising the steps of:
    providing an infusion line configured for carrying out an intravenous therapy on a patient;
    providing the infusion line with the tubing set according to claim 1;

operating a pump so as to originate a pulsating pressure in the delivery tube; and connecting the vial to the vial gate, so as to put in communication the inside of the vial both with the first lumen and with the second lumen, the first lumen being configured to deliver the drug to the delivery tube, and the second lumen being configured to provide the replacement fluid inside the vial in order to replace the delivered drug.

24. A method of delivering a drug in a hemodialysis extra-corporeal circuit, comprising the steps of:

providing a hemodialysis machine suitable for carrying out a hemodialysis treatment of a patient's blood;

providing the machine with the tubing set according to claim 1;

operating a pump so as to originate a pulsating pressure in the extra-corporeal circuit; and connecting the vial to the vial gate, so as to put in communication the inside of the vial both with the first lumen and with the second lumen, the first lumen being configured to deliver the drug to the delivery tube, and the second lumen being configured to provide the replacement fluid inside the vial in order to replace the delivered drug.

25. A method of delivering an additive in an auxiliary line, comprising the steps of:

providing an auxiliary line configured to effect a release of a liquid in a main circuit;

providing the auxiliary line with a tubing set including:

a delivery tube configured to supply the liquid to the main circuit;

a vial gate for connection of a vial containing an additive to be delivered into the liquid, the vial gate including a first lumen configured to deliver the additive from the vial to the delivery tube, and a second lumen configured to provide a replacement fluid that originates from a location inside the tubing set to the inside of the vial in order to replace the delivered additive, the vial gate including a one-way valve placed along said first lumen or said second lumen, and an element to provide for a secure connection of the vial, the element being configured to ensure a tight closure of an extra-corporeal circuit in the absence of any vial, arranged so that the connection is openable only when a vial is properly placed on the vial gate, and arranged so that the vial is removable only when the connection is closed;

operating a pump so as to originate a pulsating pressure in the delivery tube; and connecting the vial to the vial gate, so as to put in communication the inside of the vial both with the first lumen and with the second lumen, the first lumen being configured to deliver the additive to the delivery tube.

26. A method of delivering an additive in a circuit, comprising the steps of:

providing a treatment machine configured to effect a treatment of a liquid;

providing the machine with a tubing set including:

a delivery tube configured to supply the liquid to a main circuit;

a vial gate for connection of a vial containing an additive to be delivered into the liquid, the vial gate including a first lumen configured to deliver the additive from the vial to the delivery tube, and a second lumen configured to provide a replacement fluid that originates from a location inside the tubing set to the inside of the vial in order to replace the delivered additive;

the vial gate including a one-way valve placed along said first lumen or said second lumen, and an element to provide for a secure connection of the vial, the element being configured to ensure a tight closure of an extra-corporeal circuit in the absence of any vial, arranged so that the connection is openable only when a vial is properly placed on the vial gate, and arranged so that the vial is removable only when the connection is closed;

operating a pump so as to originate a pulsating pressure in the circuit; and connecting the vial to the vial gate, so as to put in communication the interior of the vial both with the first lumen and with the second lumen, the first lumen being configured to deliver the additive to the delivery tube.

* * * * *

UNITED STATES PATENT AND TRADEMARK OFFICE
CERTIFICATE OF CORRECTION

PATENT NO. : 9,623,175 B2
APPLICATION NO. : 13/696892
DATED : April 18, 2017
INVENTOR(S) : Massimo Fini et al.

It is certified that error appears in the above-identified patent and that said Letters Patent is hereby corrected as shown below:

On the Title Page

Item (73) Assignee:
Please change "Presenius Medical Care Deutschland GmbH" to -- Fresenius Medical Care Deutschland GmbH --

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*